US008293274B2

(12) United States Patent
Sakuma et al.

(10) Patent No.: US 8,293,274 B2
(45) Date of Patent: *Oct. 23, 2012

(54) INTESTINAL ABSORPTIVE ANTI-TUMOR AGENT

(75) Inventors: Shuji Sakuma, Tokyo (JP); Kiminori Atsumi, Tokyo (JP); Keiichiro Kikukawa, Tokyo (JP)

(73) Assignee: Kabushiki Kaisha Sangi, Tokyo (JP)

( * ) Notice: Subject to any disclaimer, the term of this patent is extended or adjusted under 35 U.S.C. 154(b) by 288 days.

This patent is subject to a terminal disclaimer.

(21) Appl. No.: 11/887,710

(22) PCT Filed: Apr. 5, 2006

(86) PCT No.: PCT/JP2006/307189
§ 371 (c)(1),
(2), (4) Date: Feb. 26, 2008

(87) PCT Pub. No.: WO2006/109635
PCT Pub. Date: Oct. 19, 2006

(65) Prior Publication Data
US 2009/0136577 A1    May 28, 2009

(30) Foreign Application Priority Data
Apr. 6, 2005 (JP) .................. 2005-110054

(51) Int. Cl.
*A61K 9/14* (2006.01)
(52) U.S. Cl. ..................................... 424/489
(58) Field of Classification Search .................. None
See application file for complete search history.

(56) References Cited

U.S. PATENT DOCUMENTS

| 5,443,832 | A | * | 8/1995 | Amerongen et al. ...... 424/278.1 |
| 5,512,298 | A | | 4/1996 | Aoki et al. |
| 5,603,943 | A | | 2/1997 | Yanagawa |
| 5,902,826 | A | | 5/1999 | Mogi et al. |
| 6,344,209 | B1 | | 2/2002 | Saito et al. |
| 6,541,037 | B1 | * | 4/2003 | Lee et al. ...................... 424/602 |
| 6,767,550 | B1 | | 7/2004 | Génin et al. |
| 2002/0147208 | A1 | * | 10/2002 | Fleshner-Barak et al. .... 514/283 |
| 2003/0219466 | A1 | * | 11/2003 | Kumta et al. .................. 424/423 |
| 2004/0053972 | A1 | * | 3/2004 | Nara ............................. 514/341 |
| 2004/0067257 | A1 | | 4/2004 | Bateman et al. |
| 2007/0166362 | A1 | | 7/2007 | Sakuma et al. |
| 2008/0138437 | A1 | | 6/2008 | Sakuma et al. |

FOREIGN PATENT DOCUMENTS

| EP | 0 943 336 A1 * | 9/1999 |
| EP | 1 514 538 A1 | 3/2005 |
| JP | 63-27414 A | 2/1988 |
| JP | 63-107938 A | 5/1988 |
| JP | 63-188628 A | 8/1988 |
| JP | 63-255231 | 10/1988 |
| JP | 1-51266 B2 | 11/1989 |
| JP | 2-200628 | 8/1990 |
| JP | 4-074125 | 3/1992 |
| JP | 4-112832 | 4/1992 |
| JP | 4-507106 A | 12/1992 |
| JP | 5-178762 A | 7/1993 |
| JP | 5-238956 A | 9/1993 |
| JP | 5-255095 | 10/1993 |
| JP | 6-40923 | 2/1994 |
| JP | 6-256218 A | 9/1994 |
| JP | 6-329557 | 11/1994 |
| JP | 7-2689 A | 1/1995 |
| JP | 7-101864 A | 4/1995 |
| JP | 7-165613 A | 6/1995 |
| JP | 8-20594 | 1/1996 |
| JP | 8-27031 A | 1/1996 |
| JP | 8-27174 | 1/1996 |
| JP | 8-113583 | 5/1996 |
| JP | 9-118636 A | 5/1997 |
| JP | 9-165328 | 6/1997 |
| JP | 9-166697 | 6/1997 |
| JP | 10-95738 A | 4/1998 |
| JP | 10-251285 | 9/1998 |
| JP | 11-80031 A | 3/1999 |
| JP | 2001-48865 A | 2/2001 |
| JP | 2001524937 A | 12/2001 |
| JP | 3417744 B2 | 4/2003 |
| JP | 2003-250454 A | 9/2003 |
| JP | 3471840 B2 | 9/2003 |
| JP | 2004-75662 A | 3/2004 |
| JP | 2004-143185 | 5/2004 |
| JP | 2004-307398 | 11/2004 |
| JP | 2007-45799 | 2/2007 |
| WO | WO 98/09645 | 3/1998 |
| WO | WO 98/16209 | 4/1998 |

(Continued)

OTHER PUBLICATIONS

Japanese Patent Application Kokai Publication No. (JP-A) H06-329557 (unexamined, published Japanese patent application) [Patent Document B6 ]; publication date: Nov. 29, 1994; Title: Carriers for adsorbing physiologically active substances.*
"Intraluminal administration of hydroxyapatite-carboplatin (HAp-CBDCA)," Gan to Kayaku Ryohc. 1999, p. 1791-1793, document "C2" on PTO 1449 form.*
Japanese Patent Application Kokai Publication No. H06-329557 ['557], entitled "Carriers for adsorbing physiologically active substances," designated as document "B6" in Applicants' prior art submissions.*
Mohri et al (Jpn J Cancer Chemother 26(12): 1791-1793, (1999)) (Summary) and Gan to Kayaku Ryohc. 1999. p. 1791-93 (English language translation) [Mohri]. The English language Summary is found at the end of the Japanese article. The documents were collectively designated "C2" on Applicants' submitted IDS listing.*
Japanese Patent Kokai Publication No. (JP-A) 2004-307398 [398], entitled "Multilayered microparticles enclosing pharmaceuticals," designated as document "B16" in Applicants' prior art submissions.*
WPI Accession No. 2005-075063 (XP-002497971)[online][downloaded: Oct. 17, 2008]. URL: <C:\EPOPROGS\SEA\.\..\..\epodataåsea\eplogf\internal.log.

(Continued)

*Primary Examiner* — Suzanne Ziska
(74) *Attorney, Agent, or Firm* — Hamilton, Brook, Smith & Reynolds, P.C.

(57) ABSTRACT

An objective of the present invention is to provide intestinal absorptive antitumor agents with an excellent intestinal absorptive effect by using injectable antitumor agents. In the intestinal absorptive pharmaceutical agents of the present invention, antitumor components that can be used only as injections are supported by hydroxyapatite particles.

22 Claims, 2 Drawing Sheets

FOREIGN PATENT DOCUMENTS

| | | |
|---|---|---|
| WO | WO 98/18339 A | 5/1998 |
| WO | WO 01/28587 A2 | 4/2001 |
| WO | WO 02/41844 A2 | 5/2002 |
| WO | WO 2004/041844 * | 5/2002 |
| WO | WO 2004/112751 A1 | 12/2004 |
| WO | WO 2005/074991 | 8/2005 |

OTHER PUBLICATIONS

International Search Report for PCT/JP2006307189, date of mailing Nov. 3, 2008.
"Basic studies on hyperhermic chemotherapy using adriamycin-containing hydroxyapatite", *Gan to Kagaku Ryoho*, vol. 19, No. 10, Suppl. pp. 1644-1647, Aug. 1992.
Mori, Noriaki, et al., "Gan to Kagaku Ryoho", vol. 26, No. 12, pp. 1791-1793, Oct. 1999.
Liu, Z.S., et al., "Effects of Hydroxyapatite Nanoparticles on Proliferation and Apoptosis of Human Hepatoma BEL-7402 Cells," *World .J. Gastroenterol*, 9(9): 1968-1971 (2003).
International Search Report for PCT/JP2006/307189, date of mailing Jun. 27, 2006.
Office Action from U.S. Appl. No. 10/587,966 dated Apr. 30, 2010.
Final Office Action from U.S. Appl. No. 10/587,966 dated Oct. 13, 2010.
Takahaski, et al., *Jpn J Clin Pharmacol Ther* (*Rinsho Yakuri*), 23 (1): 343-344 (1992).
International Search Report for PCT/JP2005/002771, date of mailing Apr. 5, 2005.
International Search Report, PCT/JP2005/001338, mailed May 10, 2005.
Mohri, Noriaki, et al., "Gan to Kagaku Ryoho", vol. 26, No. 12, pp. 1791-1793, Oct. 1999. (previously submitted, spelling of author's name corrected).
Aoki, H. et al., "In vitro interaction of carcinostatic substances adsorbed on hydroxyapatite microcrystals with cells derived from cancers," in *Advanced Materials '93, II / A: Biomaterials, Organic and Intelligent Materials*, H. Aoki et al., Eds (Trans. Mat. Res. Soc. Jpn., vol. 15A, 1994, Elsevier Science B.V.), pp. 3-9.

\* cited by examiner

INTESTINAL ABSORPTIVE ANTI-TUMOR AGENT

RELATED APPLICATIONS

This application is the U.S. National Stage of International Application No. PCT/JP2006/307189, filed Apr. 5, 2006, published in Japanese, and claims priority under 35 U.S.C. §119 or 365 to Japanese Application No. 2005-110054, filed Apr. 6, 2005.

TECHNICAL FIELD

The present invention relates to intestinal absorptive antitumor agents.

BACKGROUND ART

Formulations such as injections, transdermal formulations, and oral formulations are used to administer medicinal agents to the circulatory system in the body. Of these formulations, oral formulations are advantageous in that there is no pain as in injections and such, but may have low intestinal absorption depending on the type of disease or drug used for the disease. Moreover, acid in some oral formulations may decompose medicinal agents, leading to unsatisfactory efficacy. Thus, there is a need for pharmaceutical agents that enable efficient absorption of intestinal absorptive drugs such as oral formulations or suppositories. Especially in the field of antitumor agents, progress has been made in the development of various oral formulations, in addition to injections, and there is a need to develop efficient methods for using them.

Various tumors exist, such as stomach cancer, esophageal cancer, liver cancer, colon cancer, rectal cancer, pancreatic cancer, lung cancer, thyroid cancer, breast cancer, ovarian cancer, cervical cancer, endometrial cancer, ovarian cancer, tongue cancer, lip cancer, pharyngeal cancer, laryngeal cancer, oral cancer, lung cancer, skin cancer, malignant melanoma, rhabdomyosarcoma, ureteral tumor, bladder cancer, prostate cancer, testicular tumor, malignant lymphoma, leukemia, myeloma, bone tumor, nervous system tumor, and glioma.

Various antitumor agents have been developed for these tumors in chemotherapy. Specifically, antitumor agents such as the following have been developed:

alkylating agents that destroy cancer cell DNA or inhibit DNA replication by introducing an alkyl group;

antimetabolites that suppress the proliferation of cancer cells by inhibiting the metabolism of cancer cells and thereby impairing their functions;

antitumor antibiotics that are obtained from natural microorganisms and exhibit antitumor activity such as destroying the membranes of cancer cells, decomposing DNA, or inhibiting DNA synthesis;

plant preparations that stop cell division and cause cell damage by plant alkaloids obtained from plants;

hormone preparations that exhibit antitumor activity, in which hormonal agents with opposite activities, or hormonal antagonists, bind to hormone-binding sites on cancer cells in advance to the binding of hormones;

immunoadjuvants for activating the immune system;

immunotherapeutic agents that are used for regulating or enhancing immune response to cancer, such as cytokines;

platinum formulations that inhibit the cell division of cancer cells by binding to their DNA; and other antitumor agents that are not categorized as above, such as kinase inhibitors, histamine A derivatives, *Actinomyces* aminopeptidases, mannitol derivatives that exhibit activity similar to alkylating agents and antimetabolites, enzyme preparations that decompose L-asparagine in the blood and thereby render asparagine-requiring tumor cells deficient in nutrition, bisdioxopiperazine derivatives, and aceglatone which suppresses recurrent bladder tumor.

Various therapeutic methods such as surgical therapy, radiotherapy, proton beam therapy, immunotherapy, lymphocyte therapy, gene therapy, and thermotherapy have also been developed and used in combination, resulting in improved therapeutic effects.

In cancer therapy that administers antitumor agents, various formulations such as injections, oral formulations, suppositories, patches, and ointments have been developed; however, the majority of these formulations are injections and oral formulations, and in particular, most antitumor formulations are mainly injections, such as interferon and platinum antitumor agents. Absorption of antitumor agents is difficult in oral formulations, suppositories, patches, and ointments, and with oral formulations, many antitumor agents are decomposed by acids leading to unsatisfactory efficacy. Therefore, even for antitumor agents that require long-term administration, painful injections that impose a great burden on patients are inevitably used at present.

The following documents are for oral administration of antitumor agents or improvement of their efficacy by oral administration: an antitumor platinum complex that can be administered orally (Patent Documents 1 to 2), (Patent Documents 3 to 4); a hard capsule formulation of cytarabine ocfosphate for oral administration, which comprises a polymer that acts as a disintegrator and alkali (Patent Document 5); a formulation for mucosal administration, which comprises bicalutamide in a solid dispersion comprising an enteric polymer with a pKa of 3 to 6 (Patent Document 6); and a composition for oral administration comprising a dispersion/mixture of bioactive peptides in multivalent metal compound carriers (Patent Document 7).

Although not related to oral administration, the following have also been disclosed: a method for suppressing tumor growth by injecting hydroxyapatites with an average particle size of 10 to 1000 µm, to which an antitumor agent has been adsorbed, into an artery leading to a tumor site, and retaining the hydroxyapatites as a microembolus within the tumor, thereby stopping the nutrient supply to the tumor and at the same time, maintaining a high concentration of the antitumor agent at the tumor site for a long period of time (Patent Document 8); a method for controlled release of an antitumor agent by implanting into the body, hydroxyapatites with an average particle size of 100 to 500 µm filled with the antitumor agent (Patent Document 9); a method for promoting or delaying the effect of a drug, or selectively adsorbing various cells such as cancer cells, viruses such as AIDS, ATL, and hepatitis viruses and so on to control their differentiation and/or proliferation and to enable the drug to exert its effect, by adding a calcium phosphate microcrystal to the drug and administering it into the blood vessel (Patent Document 10); an invention using as a medical formulation for injection a hydroxyapatite microparticulated to 500 nm or less and whose surface has been treated by albumin and such (Patent Document 11); a calcium carbonate compound microparticle with a diameter of 0.1 to 200 µm used as an injection or a mucosal formulation such as nasal formulation, in which a biologically active substance is enclosed and whose surface is coated with a porous calcium phosphate-based-material (Patent Document 12). Also disclosed are a method for implanting into a tumor site hydroxyapatites of 1,250 to 1,500 µm to which an antitumor agent has been adsorbed, and then heating them for use in thermochemotherapy (Non-patent Document 1); and a method for controlled release of carboplatin that uses as a release-control agent, porous hydroxyapatites with an average particle size of 36.1 μm and surface area of 2.5 m$^2$/g, to prepare controlled-release carboplatin, and that administers it via an intraperitoneal or intrathoracic mediastinal route (Non-patent Document 2).

However, the absorption of antitumor agents used in oral administration is poor and in many cases the intrinsic effects of these antitumor agents are not exerted. Therefore, there is a need for pharmaceutical agents that enable efficient absorption of orally administered antitumor agents.

[Patent Document 1] Japanese Patent Application Kokai Publication No. (JP-A) H8-20594
[Patent Document 2] JP-A H8-27174
[Patent Document 3] JP-A H8-113583
[Patent Document 4] JP-A H10-251285
[Patent Document 5] JP-A H6-40923
[Patent Document 6] JP-A 2004-143185
[Patent Document 7] WO98/09645
[Patent Document 8] JP-A S63-255231
[Patent Document 9] JP-A H2-200628
[Patent Document 10] JP-A H5-255095
[Patent Document 11] JP-A H6-329557
[Patent Document 12] JP-A 2004-307398
[Non-patent Document 1] Japanese Journal of Cancer and Chemotherapy 19 (10): 1644-1647, 1992
[Non-patent Document 2] Japanese Journal of Cancer and Chemotherapy 26 (12): 1791-1793, 1999

DISCLOSURE OF THE INVENTION

Problems to be Solved by the Invention

An objective of the present invention is to provide intestinal absorptive antitumor agents with an excellent intestinal absorptive effect, which are prepared from injectable antitumor agents.

Means for Solving the Problems

Through vigorous investigations to achieve the above objective, the present inventors discovered that the intestinal absorption of antitumor components that can be used only as an injection, can be enhanced by using hydroxyapatite particles to support these components. Specifically, the present invention comprises the following:

[1] an intestinal absorptive antitumor agent, in which an injectable antitumor component is supported by hydroxyapatite particles

[2] the intestinal absorptive antitumor agent of [1], wherein said hydroxyapatite has a maximum particle size of 10 μm or less;

[3] the intestinal absorptive antitumor agent of [1] or [2], wherein said hydroxyapatite has a maximum particle size of 0.5 μm or less;

[4] the intestinal absorptive antitumor agent of any one of [1] to [3], wherein said hydroxyapatite has a maximum particle size of 0.1 μm or less;

[5] the intestinal absorptive antitumor agent of any one of [1] to [4], wherein the content of said hydroxyapatite is 0.5 to 5000 weight percent of the injectable antitumor component;

[6] the intestinal absorptive antitumor agent of any one of [1] to [5], wherein said injectable antitumor component is a platinum preparation, cytokine, alkylating agent, antimetabolite, antitumor antibiotic, plant preparation, immunotherapeutic agent, kinase inhibitor, enzyme preparation, histamine A derivative, aminopeptidase, mannitol derivative, bisdioxopiperazine derivative, inhibitor of recurrent bladder tumor, or therapeutic agent for cancer pain;

[7] the intestinal absorptive antitumor agent of [6], wherein said platinum preparation is selected from the group consisting of cisplatin, carboplatin, and nedaplatin; said cytokine is an interferon; said alkylating agent is selected from the group consisting of ranimustine, nimustine hydrochloride, ifosfamide, dacarbazine, and thiotepa; said antimetabolite is selected from the group consisting of gemcitabine hydrochloride, cytarabine, enocitabine, fludarabine phosphate, calcium levofolinate, vincristine sulfate, and vinblastine sulfate; said antitumor antibiotic is selected from the group consisting of peplomycin sulfate, pirarubicin hydrochloride, zinostatin stimalamer, idarubicin hydrochloride, mitomycin C, bleomycin hydrochloride, doxorubicin hydrochloride, daunorubicin hydrochloride, and epirubicin hydrochloride; said plant preparation is selected from the group consisting of vindesine sulfate, vinorelbine ditartrate, irinotecan hydrochloride, nogitecan hydrochloride, docetaxel hydrate, and paclitaxel;

[8] the intestinal absorptive antitumor agent of any one of [1] to [7], wherein said hydroxyapatite is an amorphous hydroxyapatite;

[9] use of a hydroxyapatite particle that supports an injectable antitumor component for preparing an intestinal absorptive antitumor agent; and

[10] a method for treating a tumor, which comprises administering an effective amount of the intestinal absorptive antitumor agent of [1] to a patient in need of prevention or treatment of the tumor.

The hydroxyapatites used in the present application are usually indicated by the stoichiometric composition $Ca_{10}(PO_4)_6(OH)_2$; however, even in non-stoichiometric cases in which the mole ratio of Ca/P is not 1.67, they show characteristics of hydroxyapatite and can take an apatite structure.

In the present invention, hydroxyapatites that have a stoichiometric composition or non-stoichiometric composition can be used, and those with a Ca/P mole ratio of 1.4 to 1.8 can be used.

The Ca/P mole ratio of a hydroxyapatite can be controlled by regulating the mixture ratio of ingredient salts and synthesis conditions. For example, in the wet synthesis of hydroxyapatite, adjusting the solution to basic conditions with aqueous ammonia results in a high Ca/P mole ratio, while adjusting the solution to neutral or weakly acid conditions with dilute acid can results in a low Ca/P mole ratio.

Crystalline hydroxyapatites, poorly crystalline hydroxyapatites, and noncrystalline hydroxyapatites can be used as hydroxyapatites in the present invention; however, poorly crystalline or noncrystalline hydroxyapatites are preferred. Intestinal absorption is further enhanced by the use of poorly crystalline or noncrystalline hydroxyapatites.

In the present invention, "poorly crystalline" means a crystalline powder shows a broader X-ray diffraction peak compared to a highly crystalline powder. "Noncrystalline" means a powder that shows an even broader X-ray diffraction peak than poorly crystalline powders and does not exhibit a clear diffraction pattern characteristic of a crystal. Hereinafter, poorly crystalline hydroxyapatites and noncrystalline hydroxyapatites will be referred to as "amorphous hydroxyapatites".

The amorphous hydroxyapatites used in the present invention include, for example, hydroxyapatites prepared by wet synthesis as mentioned above and then freeze dried, or dried at a temperature of 100° C. or below, or baked at a temperature of about 300° C. or below.

The hydroxyapatite particles used in the present invention, when used for a general oral formulation, preferably have a maximum particle size of 10 μm or less (average particle size of 7 μm or less), more preferably a maximum particle size of 5 μm or less (average particle size of 3 μm or less). When used as enteric capsules or enteric coated formulations, particles preferably have a maximum particle size of 0.5 μm or less (average particle size of 0.3 μm or less), and more preferably a maximum particle size of 0.1 μm or less (average particle size of 0.07 μm or less).

The smaller the particle size, the larger the specific area surface is thus increased capability to adsorb drugs. There is no minimum limitation on the average particle size; however, the minimum average particle size is preferably about 0.01 μm.

In addition, when considering the dissolution of the hydroxyapatites supporting an antitumor agent by gastric acid, for example, an average particle size of 0.2 μm or more is preferred.

When used as enteric capsules or enteric coated formulations, there is no particular limitation as there is no dissolution by gastric acid; however, for manufacturing reasons, the maximum particle size is preferably 0.5 μm or less (average particle size is about 0.2 μm), and more preferably 0.1 μm or less (average particle size is about 0.05 μm).

Hydroxyapatite particles with a maximum particle size of 10 μm or less, 5 μm or less, 0.5 μm or less, and 0.1 μm or less can be prepared by grinding. Various antitumor components with added hydroxyapatites can be prepared by methods such as grinding hydroxyapatites and then mixing them with various antitumor components, or using hydroxyapatites to support antitumor components and then grinding.

Powder or solid antitumor components are dissolved or dispersed, supported by hydroxyapatites, and then grinded, although they can also be used by directly mixing with hydroxyapatites.

For antitumor components supported by hydroxyapatites, it is preferred that the dissolved or dispersed antitumor components are supported by grinded hydroxyapatites.

Antitumor components that have been dissolved or dispersed in solvents compatible with oral administration, such as distilled water or physiological saline, may be supported by hydroxyapatites and then used as they are, or may be used after drying. However, in consideration of the toxicity of various antitumor agents, antitumor components that have been dissolved or dispersed in other solvents are preferably used after solvent is removed by drying the obtained antitumor agent solution and such.

In the present invention, "intestinal absorption" refers to absorption through the intestinal wall, and "intestinal absorptive antitumor agents" refer to antitumor agents that are intestinally absorbed regardless of their method of administration.

In the present invention, the method of administering compositions is not particularly limited, as long as the mode of drug absorption is intestinal absorption; however, oral administration is preferred.

As used herein, the above "antitumor components are supported by hydroxyapatites" refers to a condition in which the hydroxyapatite particle surface is coated with an antitumor component and the antitumor component is permeated into the pores of hydroxyapatites.

The content of hydroxyapatites that support an antitumor component depends on the type of antitumor component, and would be difficult to be determined indiscriminately; however, it is preferably 0.5 to 5000 weight percent, more preferably 1 to 1000 weight percent of the medicinal agent, and it is preferably 1 to 500 weight percent of the antitumor component dose.

The antitumor components that can be used in the present invention are for example, platinum preparations, cytokine, alkylating agents, antimetabolites, antitumor antibiotics, plant preparations, immunotherapeutic agents, kinase inhibitors, enzyme preparations, histamine A derivatives, aminopeptidases, mannitol derivatives, bisdioxopiperazine derivatives, inhibitors of recurrent bladder tumor, and therapeutic agents for cancer pain. The antitumor components of the present invention are injectable antitumor components.

The above-mentioned antitumor compositions can include, but are not limited to, the following:

platinum preparations such as cisplatin, carboplatin, and nedaplatin; cytokines such as interferon, alkylating agents such as ranimustine, nimustine hydrochloride, ifosfamide, dacarbazine, and thiotepa; antimetabolites such as gemcitabine hydrochloride, cytarabine, enocitabine, fludarabine phosphate, calcium levofolinate, vincristine sulfate, and vinblastine sulfate; antitumor antibiotics such as peplomycin sulfate, pirarubicin hydrochloride, zinostatin stimalamer, idarubicin hydrochloride, mitomycin C, bleomycin hydrochloride, doxorubicin hydrochloride, daunorubicin hydrochloride, and epirubicin hydrochloride; plant preparations such as vindesine sulfate, vinorelbine ditartrate, irinotecan hydrochloride, nogitecan hydrochloride, docetaxel hydrate, and paclitaxel.

For the above-mentioned antitumor components, cytokines or platinum preparations are preferred; interferon β is particularly preferred among cytokines, and cisplatin is particularly preferred among platinum preparations.

The above-mentioned antitumor components for injection are antitumor components that are administered by intradermal injection, subcutaneous injection, intramuscular injection, intravenous injection, or intravenous drip infusion, in the current medical environment.

By combining the hydroxyapatites of the present invention with the above-mentioned antitumor components, it is possible to improve the absorptivity of injectable antitumor components considerably without any decomposition by gastric acid and such.

In the present invention, the above-mentioned antitumor components which are used as injections can be made into oral formulations that are absorbed intestinally.

According to the present invention, it is possible to enhance the intestinal absorption of various injectable antitumor components, and therefore provide oral formulations that make the best of the intrinsic effect of these medicinal components.

The dosage forms used in the present invention can be those for intestinal absorption, such as tablets, capsules, powders, granules, and liquids.

As used herein, "enteric coated capsules" refers to capsules in which tablets or capsules of pharmaceutical agents are coated with substances that dissolve after reaching the small intestine, and "enteric coating" refers to coating a pharmaceutical agent with such a substance.

The dosage of the intestinal absorptive compositions of the present invention can be suitably chosen according to the degree of symptoms, age, gender, body weight, administration form, specific type of disease and such. The daily dosage for an adult is usually about 0.03 mg to 1000 mg, preferably 0.1 mg to 500 mg, or more preferably 0.1 mg to 100 mg, which is administered in one to several separate doses.

Another embodiment of the present invention is the use of medicinal components and hydroxyapatites for preparing intestinal absorptive antitumor agents.

The methods for preventing or treating diseases of the present invention comprise administering effective amounts of the above-mentioned intestinal absorptive antitumor components and hydroxyapatites.

For the antitumor components and hydroxyapatites, the above-mentioned medicinal components and hydroxyapatites can be preferably used.

All prior art documents cited herein are incorporated herein by reference.

MODES FOR CARRYING OUT THE INVENTION

Examples

Herein below, the present invention will be described with reference to Examples, but it is not to be construed as being limited thereto.

Preparation Example 1

Production of Amorphous Hydroxyapatites

Phosphoric acid solution of 30 weight percent concentration was added dropwise to a suspension of calcium hydroxide with stirring until the pH reached 10, and the resulting gel was left to stand at room temperature for one day to mature. The gel was then filtered through a glass filter and the residue was dried in air at 100° C. to give amorphous hydroxyapatites with the diffraction pattern shown at the bottom of FIG. 1.

Preparation Example 2

Production of Crystalline Hydroxyapatites

Figure 1:
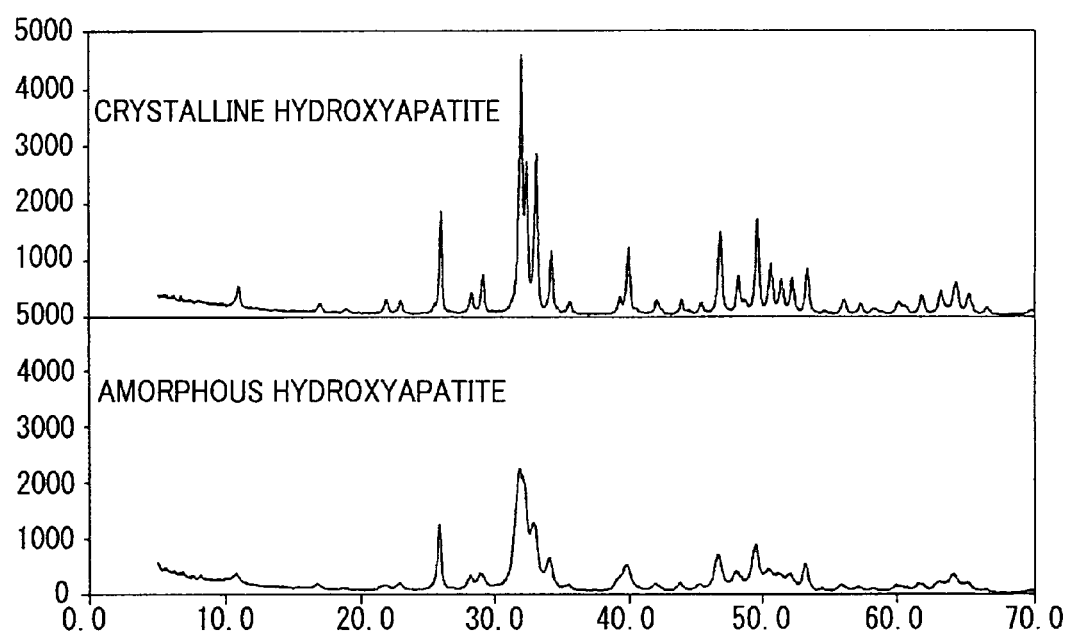
FIG. 1 shows the powder X-ray diffraction pattern of crystalline hydroxyapatites and amorphous hydroxyapatites.

A portion of the amorphous hydroxyapatites prepared in Preparation Example 1 was dried in air at 80° C., and then baked for 2 hours to give crystalline hydroxyapatites with the diffraction pattern shown at the top of FIG. 1.

Preparation of Various Antitumor Agents Supplemented with Hydroxyapatite

Example 1-1

Cisplatin was dissolved in N,N-dimethylformamide, and to this solution, a given amount of amorphous hydroxyapatites ground to a maximum particle size of 10 μm or less with a jet mill (Co-Jet system α-mkII, manufactured by Seishin Enterprise Co., Ltd) was added. The solution was stirred at room temperature overnight under reduced pressure. The solution was dried under negative pressure to give a desolventized antitumor cisplatin powder supplemented with ground hydroxyapatites with a maximum particle size of 10 μm or less (average particle size is about 5 μm) (Example 1-1).

Example 1-2

Instead of amorphous hydroxyapatites ground to a maximum particle size of 10 μm or less, amorphous hydroxyapatites ground to a maximum particle size of 5 μm or less were used in the similar method to the above to give a desolventized antitumor cisplatin powder supplemented with ground hydroxyapatites with a maximum particle size of 5 μm or less (average particle size is about 2 μm) (Example 1-2).

Examples 1-3 and 1-4

Two weight percent of amorphous hydroxyapatite was added to distilled water and ground using a Dyno-Mill (ECM-PILOT manufactured by Willy A. Baechofen AG Machinenfabrik Basel). Grinding was carried out at a temperature of 5° C. or below by using a cooling circulating pump. Particle size was measured and when the maximum particle size became 0.5 μm or less, a portion of the solution was taken out and dried under negative pressure to give amorphous hydroxyapatite microparticles with a maximum particle size of 0.5 μm or less. The remaining solution was further ground and when the maximum particle size became 0.1 μm or less, the grinding was stopped and the solution was dried under negative pressure to give amorphous hydroxyapatite microparticles with a maximum particle size of 0.1 μm or less.

Cisplatin was dissolved in N,N-dimethylformamide, and to this solution, given amounts of amorphous hydroxyapatite microparticles with a maximum particle size of 0.5 μm or less and amorphous hydroxyapatite microparticles with a maximum particle size of 0.1 μm or less prepared above were individually added. The solutions were stirred at room temperature overnight under reduced pressure. The solutions were dried under negative pressure to give desolventized antitumor cisplatin powders supplemented with ground hydroxyapatites with a maximum particle size of 5 μm or less (average particle size is about 0.2 μm) (Example 1-3), and ground hydroxyapatites with a maximum particle size of 0.1 μm or less (average particle size is about 0.05 μm).

In addition, an enteric coating solution prepared by mixing cellulose acetate phthalate, diethyl phthalate, and acetone at a volume ratio of 36:9:255 was sprayed onto the antitumor cisplatin powder supplemented with ground amorphous hydroxyapatites with a maximum particle size of 0.1 μm or less, and then dried under negative pressure to give an enteric formulation.

Examples 1-5 and 1-6

Similarly to the above, crystalline hydroxyapatites were ground to a maximum particle size of 5 μm or less by a jet-mill, or to a maximum particle size of 0.5 μm or less with a Dyno-Mill, and used in place of the above amorphous hydroxyapatites to produce antitumor powders. Antitumor cisplatin powders supplemented with ground crystalline hydroxyapatites with a maximum particle size of 5 μm or less (average particle size is about 2 μm) or a maximum particle size of 0.5 μm or less (average particle size is about 0.2 μm) were obtained (Examples 1-5 and 1-6).

Reference Example 1

In addition, by a similar method to the above, tricalcium phosphate was used instead of amorphous hydroxyapatites to prepare tricalcium phosphate microparticles with a maximum particle size of 0.5 μm or less using a Dyno-Mill. Antitumor cisplatin powder supplemented with ground tricalcium phosphate with a maximum particle size of 0.5 μm or less (average particle size is about 0.2 μm) was obtained by a similar method to the above (Reference Example 1).

Examples 1-7 to 1-10

Two weight percent of amorphous hydroxyapatites was added to distilled water, and given amounts of various antitumor agents such as interferon A, ifosfamide, bleomycin hydrochloride, and vincristine sulfate were each added, and then the solutions were stirred under reduced pressure. These antitumor solutions were ground at a temperature of 5° C. or below with a Dyno-Mill using a cooling circulating pump. After grinding, these various antitumor solutions were dried to give various antitumor powders supplemented with ground hydroxyapatites with a maximum particle size of 0.4 μm to 0.5 μm (average particle size is about 0.2 μm).

The content of hydroxyapatite in the various antitumor agents prepared for intestinal absorption test is shown in Table 1. The amount of hydroxyapatite added is represented as the ratio (weight percent) of hydroxyapatite to antitumor agent.

TABLE 1

| Example | Antitumor agent | Amount of hydroxyapatite added (%) | | | |
|---|---|---|---|---|---|
| | | -1 | -2 | -3 | -4 |
| Example 1-1 | Cisplatin | 1 | 100 | 500 | 1000 |
| Example 1-2 | Cisplatin | 1 | 100 | 500 | 1000 |
| Example 1-3 | Cisplatin | 1 | 100 | 500 | 1000 |
| Example 1-4 | Cisplatin | 0.5 | 10 | 100 | 500 |

| | | -5 | -6 |
|---|---|---|---|
| | | 1000 | 5000 |

| Example | Antitumor agent | -1 | -2 | -3 | -4 |
|---|---|---|---|---|---|
| Example 1-5 | Cisplatin | 1 | 100 | 500 | 1000 |
| Example 1-6 | Cisplatin | 1 | 100 | 500 | 1000 |
| Example 1-7 | Interferonβ | 1 | 100 | 500 | 1000 |
| Example 1-8 | Ifosfamide | 1 | 100 | 500 | 1000 |
| Example 1-9 | Bleomycin hydrochloride | 1 | 100 | 500 | 1000 |
| Example 1-10 | Vincristine sulfate | 1 | 100 | 500 | 1000 |
| Reference Example 1 | Cisplatin | 1 | 100 | 500 | 1000 |

Comparative Test of Intestinal Absorption of Cisplatin Supplemented with Hydroxyapatites Test Examples 1-1-1 to 1-1-4, Test Examples 1-2-1 to 1-2-4, Test Examples 1-4-1 to 1-4-6, and Test Examples 1-5-1 to 1-5-4

Samples for Test Examples 1-1-1 to 1-1-4, Test Examples 1-2-1 to 1-2-4, Test Examples 1-4-1 to 1-4-6, and Test Examples 1-5-1 to 1-5-4 were orally administered to Sprague-Dawley male rats (7 weeks old). The rats were well fed and forced oral administration to the stomach was performed using an oral gastric tube for rats.

Test Examples 1-3-1 to 1-3-4, Test Examples 1-6-1 to 1-6-4, Reference Test Examples 1-1 to 1-4

Samples of Test Examples 1-3-1 to 1-3-4, Test Examples 1-6-1 to 1-6-4, and Reference Test Examples 1-1 to 1-4 were orally administered to Sprague-Dawley male rats (7 weeks old). To pass the antitumor agents through the stomach without being dissolved by gastric acid, the rats were fasted for 16 hours and then forced oral administration to the stomach was performed using an oral gastric tube for rats.

In all Test Examples and Reference Test Examples, the dosage of cisplatin was 30 mg/kg.

Comparative Test Examples 1-1 to 1-2

As a comparison, the same dosage of cisplatin was orally administered by the same method as above to rats after they had been fasted for 16 hours (Comparative Test Example 1-1). As an additional comparison, 2 mg/kg of cisplatin was intravascularly administered (Comparative Test Example 1-2).

The administered sample of cisplatin used for comparison was prepared by lightly grinding in an agate mortar and then adding distilled water.

The blood was collected from the tail vein prior to administration and 30 minutes, 1, 2, 3, 6, 10, 16, and 24 hours after administration. The blood collected was centrifuged at 4° C. for 15 minutes at 3,000 rpm to obtain plasma, and it was stored at −35° C. until the cisplatin concentration in the plasma was measured. The cisplatin concentration in the plasma was measured using ICP, and the results are shown in Table 2.

Figure 2:
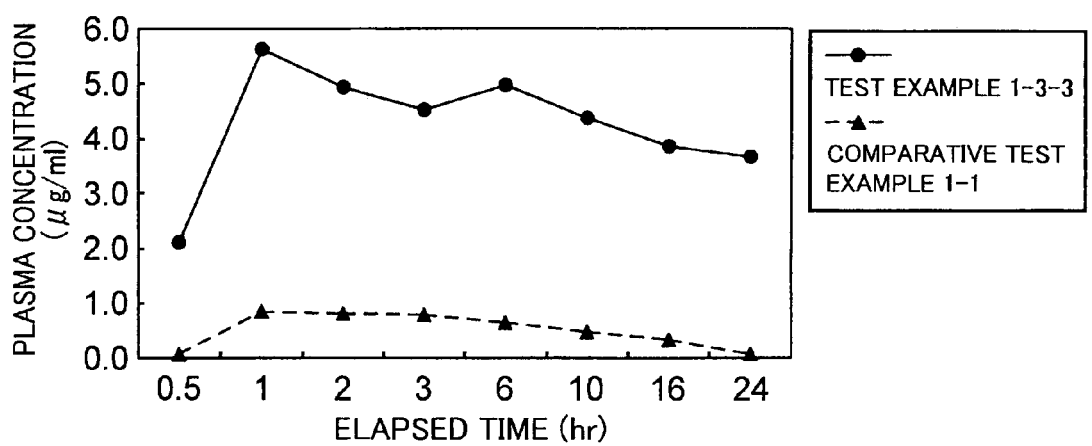
FIG. 2 is a graph showing a time course of the cisplatin concentration in crystals.

FIG. 2 shows a time course of the cisplatin concentration in plasma in Test Example 1-3-3 and Comparative Test Example 1-1.

The blood concentrations of medicinal agents absorbed into the body through the intestinal walls can be usually measured by collecting blood from the tail vein.

TABLE 2

| | $AUC_{0-24h}$ μg/h/ml | Cmax μg/ml | Tmax h |
|---|---|---|---|
| Test Example 1-1-1 | 25.52 | 2.04 | 1.17 |
| Test Example 1-1-2 | 53.57 | 2.51 | 6.33 |
| Test Example 1-1-3 | 57.34 | 2.70 | 4.67 |
| Test Example 1-1-4 | 41.01 | 1.93 | 4.33 |
| Test Example 1-2-1 | 49.75 | 2.33 | 2.83 |
| Test Example 1-2-2 | 81.43 | 4.11 | 2.33 |
| Test Example 1-2-3 | 89.32 | 4.49 | 2.17 |
| Test Example 1-2-4 | 51.75 | 2.94 | 2.50 |
| Test Example 1-3-1 | 61.57 | 3.45 | 2.50 |
| Test Example 1-3-2 | 89.72 | 4.43 | 2.17 |
| Test Example 1-3-3 | 100.06 | 4.97 | 2.83 |
| Test Example 1-3-4 | 56.32 | 2.77 | 3.83 |
| Test Example 1-4-1 | 44.30 | 2.41 | 2.50 |
| Test Example 1-4-2 | 73.32 | 3.41 | 3.00 |
| Test Example 1-4-3 | 99.03 | 4.96 | 2.33 |
| Test Example 1-4-4 | 112.90 | 5.65 | 2.83 |
| Test Example 1-4-5 | 63.43 | 2.86 | 3.67 |
| Test Example 1-4-6 | 55.33 | 2.70 | 6.33 |
| Test Example 1-5-1 | 36.08 | 2.18 | 2.50 |
| Test Example 1-5-2 | 69.59 | 4.05 | 1.67 |
| Test Example 1-5-3 | 78.88 | 4.52 | 2.50 |
| Test Example 1-5-4 | 42.68 | 2.14 | 2.50 |
| Test Example 1-6-1 | 53.58 | 3.01 | 1.67 |
| Test Example 1-6-2 | 80.56 | 3.94 | 2.17 |
| Test Example 1-6-3 | 87.37 | 4.26 | 2.33 |
| Test Example 1-6-4 | 48.76 | 2.27 | 6.33 |
| Reference Test Example 1-1 | 0.02 | 0.01 | 1.00 |
| Reference Test Example 1-2 | 0.21 | 0.02 | 1.42 |
| Reference Test Example 1-3 | 0.43 | 0.03 | 1.25 |
| Reference Test Example 1-4 | 0.11 | 0.02 | 1.17 |
| Comparative Test Example 1-1 | 10.35 | 0.84 | 1.08 |
| Comparative Test Example 1-2 | 30.70 | 5.93 | 0.58 |

Table 2 shows that the antitumor cisplatin agents supplemented with hydroxyapatites with a maximum particle size of 0.5 μm or less are greatly superior in intestinal absorptivity.

It is also shown that the nonenteric-coated antitumor cisplatin agents supplemented with hydroxyapatites have the same level of intestinal absorptivity as the enteric-coated antitumor cisplatin agents supplemented with hydroxyapatites (with a maximum particle size of 0.1 μm).

Moreover, the intestinal absorptivity of the antitumor cisplatin agents supplemented with hydroxyapatites prepared using amorphous hydroxyapatites is found to be higher than that of the antitumor cisplatin agents supplemented with hydroxyapatites prepared using crystalline hydroxyapatites.

In addition, the antitumor cisplatin agent supplemented with tricalcium phosphate, which was prepared as a reference example using tricalcium phosphate, showed the same level of intestinal absorption as the cisplatin administered for comparison.

Intestinal Absorption Test of Various Antitumor Agents

Test Examples 4-7 to 4-10, Comparative Test Examples 4-1 to 4-4

Samples of Examples 1-7-1, 1-8-2, 1-9-3, and 1-10-4 were orally administered to Sprague-Dawley male rats (7 weeks old). Rats were fasted for 16 hours and then forced oral administration to the stomach was performed using an oral gastric tube for rats.

The dosages were as follows: 1 million units/kg of interferon β, 50 mg/kg of ifosfamide, 2.0 mg/kg of bleomycine hydrochloride, and 0.2 mg/kg of vincristine sulfate (Test Example 4-7 (interferon β), Test Example 4-8 (ifosfamide), Test Example 4-9 (bleomycine hydrochloride), and Test Example 4-10 (vincristine sulfate)).

For comparison, various antitumor agents of the same dosage were orally administered by the same method as above after the rats were fasted for 16 hours (Comparative Test Examples 4-1 (interferon β), 4-2 (ifosfamide), 4-3 (bleomycin hydrochloride), and 4-4 (vincristine sulfate)).

Samples of the various antitumor agents administered for comparison (interferon β, ifosfamide, bleomycin hydrochloride, and vincristine sulfate) were prepared by lightly grinding in an agate mortar and then adding distilled water.

Blood was collected from the tail vein prior to administration and 15 and 30 minutes, 1, 2, 3, 4, 6, 8 and 24 hours after administration. The collected blood was centrifuged at 4° C. for 15 minutes at 3,000 rpm to obtain plasma, and then the plasma concentrations of the various antitumor agents were measured.

These concentrations were measured using gas chromatography and liquid chromatography. The results are shown in Table 3.

TABLE 3

|  | $AUC_{0-24h}$ IU hr/ml | Cmax IU/ml | Tmax hr |
|---|---|---|---|
| Test Example 4-7 | 60.7 | 19.03 | 3.33 |
|  | μg hr/ml | μg/ml | hr |
| Test Example 4-8 | 1.93 | 0.30 | 2.33 |
| Test Example 4-9 | 1.26 | 0.32 | 3.83 |
| Test Example 4-10 | 1.87 | 0.19 | 3.00 |
|  | IU hr/ml | IU/ml | hr |
| Comparative Test Example 4-1 | 3.79 | 1.52 | 1.50 |
|  | μg hr/ml | μg/ml | hr |
| Comparative Test Example 4-2 | 1.24 | 0.25 | 0.75 |
| Comparative Test Example 4-3 | 0.52 | 0.12 | 1.42 |
| Comparative Test Example 4-4 | 1.11 | 0.09 | 0.83 |

These results show that intestinal absorption increases when hydroxyapatites, in particular amorphous hydroxyapatites, are added to various antitumor components.

INDUSTRIAL APPLICABILITY

The present invention can provide oral formulations in which various injectable antitumor components have an enhanced intestinal absorptivity.

The invention claimed is:

1. An intestinal absorptive antitumor composition comprising an injectable antitumor agent coating the surface of and permeating into the pores of hydroxyapatite particles, wherein said hydroxyapatite particles are provided in a maximum particle size of 0.5 μm or less and in an amount sufficient to increase plasma concentration of said injectable antitumor agent administered orally to a subject as compared to the injectable antitumor agent administered orally without said hydroxyapatite particles.

2. The intestinal absorptive antitumor composition of claim 1, wherein said hydroxyapatite has a maximum particle size of 0.1 μm.

3. The intestinal absorptive antitumor composition of claim 1, wherein the content of said hydroxyapatite is 0.5 to 5000 weight percent of the injectable antitumor agent.

4. The intestinal absorptive antitumor composition of claim 1, wherein said injectable antitumor agent is a platinum preparation, cytokine, alkylating agent, antimetabolite, antitumor antibiotic, plant preparation, immunotherapeutic agent, kinase inhibitor, enzyme preparation, histamine A derivative, aminopeptidase, mannitol derivative, bisdioxopiperazine derivative, inhibitor of recurrent bladder tumor, or therapeutic agent for cancer pain.

5. The intestinal absorptive antitumor composition of claim 3, wherein the injectable antitumor agent is a platinum preparation comprising one or more of cisplatin, carboplatin, and/or nedaplatin.

6. The intestinal absorptive antitumor composition of claim 1, wherein said hydroxyapatite is an amorphous hydroxyapatite.

7. A method for treating a tumor comprising, administering an effective amount of the intestinal absorptive antitumor composition of claim 1 to a patient in need of treatment of the tumor.

8. The intestinal absorptive antitumor composition of claim 2, wherein said intestinal absorptive antitumor composition is an enteric coated capsule or tablet.

9. A method for increasing intestinal absorption of an injectable antitumor agent in a patient comprising orally administering to the patient the composition of claim 1.

10. The intestinal absorptive antitumor composition of claim 3, wherein said injectable agent comprises an interferon.

11. The intestinal absorptive antitumor composition of claim 3, wherein said injectable agent is an alkylating agent comprising one or more of ranimustine, nimustine hydrochloride, ifosfamide, dacarbazine, and/or thiotepa.

12. The intestinal absorptive antitumor composition of claim 3, wherein said injectable agent is an antimetabolite comprising one or more of gemcitabine hydrochloride, cytarabine, enocitabine, fludarabine phosphate, calcium levofolinate, vincristine sulfate, and/or vinblastine sulfate.

13. The intestinal absorptive antitumor composition of claim 3, wherein said injectable agent is an antitumor antibiotic comprising one or more of peplomycin sulfate, pirarubicin hydrochloride, zinostatin stimalamer, idarubicin hydrochloride, mitomycin C, bleomycin hydrochloride, doxorubicin hydrochloride, daunorubicin hydrochloride, and/or epirubicin hydrochloride.

14. The intestinal absorptive antitumor composition of claim 3, wherein said injectable agent is a plant preparation comprising one or more of vindesine sulfate, vinorelbine ditartrate, irinotecan hydrochloride, nogitecan hydrochloride, docetaxel hydrate, and/or paclitaxel.

15. The intestinal absorptive antitumor composition of claim 2, wherein said intestinal absorptive antitumor composition is provided without enteric coating.

16. The method of claim 9, wherein the injectable antitumor agent is provided without enteric coating.

17. The intestinal absorptive antitumor composition of claim 3, wherein the content of said hydroxyapatite is 100-1000 weight percent of the injectable antitumor agent.

18. The composition of claim 17, wherein the hydroxyapatite is an amorphous hydroxyapatite.

19. A method for treating a tumor in a patient comprising orally administering to the patient a therapeutically effective amount of the composition of claim 18.

20. An intestinal absorptive antitumor composition comprising an injectable antitumor agent coating the surface of and permeating into the pores of hydroxyapatite particles, wherein said hydroxyapatite particles are provided in a maximum particle size of 0.5 µm or less and in an amount sufficient to increase plasma concentration of said injectable antitumor agent administered orally to a subject as compared to the injectable antitumor agent administered orally without said hydroxyapatite particles, wherein the injectable antitumor agent is not a protein.

21. The composition of claim 17, wherein the antitumor agent is selected from the group consisting of a platinum preparation comprising one or more of cisplatin, carboplatin, and/or nedaplatin; an alkylating agent comprising one or more of ranimustine, nimustine hydrochloride, ifosfamide, dacarbazine, and/or thiotepa; an antimetabolite comprising one or more of gemcitabine hydrochloride, cytarabine, enocitabine, fludarabine phosphate, calcium levofolinate, vincristine sulfate, and/or vinblastine sulfate; an antitumor antibiotic comprising one or more of peplomycin sulfate, pirarubicin hydrochloride, zinostatin stimalamer, idarubicin hydrochloride, mitomycin C, bleomycin hydrochloride, doxorubicin hydrochloride, daunorubicin hydrochloride, and/or epirubicin hydrochloride; and a plant preparation comprising one or more of vindesine sulfate, vinorelbine ditartrate, irinotecan hydrochloride, nogitecan hydrochloride, docetaxel hydrate, and/or paclitaxel.

22. An intestinal absorptive antitumor composition comprising an injectable antitumor agent coating the surface of and permeating into the pores of amorphous hydroxyapatite particles, wherein said amorphous hydroxyapatite particles are provided in a maximum particle size of 0.5 µm or less and in an amount sufficient to increase plasma concentration of said injectable antitumor agent administered orally to a subject as compared to the injectable antitumor agent administered orally without said amorphous hydroxyapatite particles, wherein the injectable antitumor agent selected from the group consisting of interferon β; a platinum preparation comprising one or more of cisplatin, carboplatin, and/or nedaplatin; an alkylating agent comprising one or more of ranimustine, nimustine hydrochloride, ifosfamide, dacarbazine, and/or thiotepa; an antimetabolite comprising one or more of gemcitabine hydrochloride, cytarabine, enocitabine, fludarabine phosphate, calcium levofolinate, vincristine sulfate, and/or vinblastine sulfate; an antitumor antibiotic comprising one or more of peplomycin sulfate, pirarubicin hydrochloride, zinostatin stimalamer, idarubicin hydrochloride, mitomycin C, bleomycin hydrochloride, doxorubicin hydrochloride, daunorubicin hydrochloride, and/or epirubicin hydrochloride; and a plant preparation comprising one or more of vindesine sulfate, vinorelbine ditartrate, irinotecan hydrochloride, nogitecan hydrochloride, docetaxel hydrate, and/or paclitaxel, and wherein the content of said amorphous hydroxyapatite is 100-1000 weight percent of the injectable antitumor agent.

* * * * *